(12) United States Patent
Fiechter et al.

(10) Patent No.: US 10,874,441 B2
(45) Date of Patent: Dec. 29, 2020

(54) OCCIPITAL-CERVICAL FIXATION EQUIPMENT

(71) Applicant: MEDACTA INTERNATIONAL S.A., Castel San Pietro (CH)

(72) Inventors: Meinrad Fiechter, Lugano (CH); Michele Incandela, Como (IT); Massimiliano Martis, Cassina Rizzardi (IT); Francesco Siccardi, Castel San Pietro (CH)

(73) Assignee: MEDACTA INTERNATIONAL S.A., Castel San Pietro (CH)

( * ) Notice: Subject to any disclaimer, the term of this patent is extended or adjusted under 35 U.S.C. 154(b) by 56 days.

(21) Appl. No.: 15/781,124

(22) PCT Filed: Nov. 24, 2016

(86) PCT No.: PCT/IB2016/057103
§ 371 (c)(1),
(2) Date: Jun. 2, 2018

(87) PCT Pub. No.: WO2017/093863
PCT Pub. Date: Jun. 8, 2017

(65) Prior Publication Data
US 2018/0353218 A1 Dec. 13, 2018

(30) Foreign Application Priority Data

Dec. 3, 2015 (IT) .................. 102015000080059

(51) Int. Cl.
*A61B 17/70* (2006.01)
*A61B 17/80* (2006.01)

(52) U.S. Cl.
CPC ...... *A61B 17/7055* (2013.01); *A61B 17/8033* (2013.01)

(58) Field of Classification Search
CPC ............ A61B 17/7032; A61B 17/7034; A61B 17/7049; A61B 17/705; A61B 17/7055
See application file for complete search history.

(56) References Cited

U.S. PATENT DOCUMENTS

2010/0023058 A1* 1/2010 Tornier ............. A61B 17/7049
606/246
2011/0087288 A1 4/2011 Stevenson et al.
(Continued)

OTHER PUBLICATIONS

International Search Report for PCT/IB2016/057103, Feb. 24, 2017, 2 pages.

*Primary Examiner* — Eduardo C Robert
*Assistant Examiner* — Christina Negrellirodriguez
(74) *Attorney, Agent, or Firm* — Meunier Carlin & Curfman LLC (57) ABSTRACT

Occipital-cervical fixation equipment comprising: an occipital plate able to be fixed to an occipital portion of the skull of a patient; at least two longitudinal lateral bars able to be arranged in a sagittal direction alongside the spinous processes of the vertebrae of the patient, each longitudinal lateral bar extending between an occipital end portion and a vertebral end portion; a first fixation means configured to fix the occipital end portion of each longitudinal lateral bar and the occipital plate; a second fixation means configured to fix the longitudinal lateral bars to a patient's vertebra; a transverse connector; the third fixation means configured to fix the occipital end portion of the longitudinal central bar to the occipital plate; and the fourth fixation means configured to fix the lateral end portions of the cross bar respectively to one of two longitudinal lateral bars. Other aspects are disclosed and claimed.

20 Claims, 8 Drawing Sheets (56) References Cited

U.S. PATENT DOCUMENTS

| | | |
|---|---|---|
| 2013/0053892 A1 | 2/2013 | Hawkins et al. |
| 2013/0184762 A1 | 7/2013 | Harper et al. |
| 2013/0238033 A1 | 9/2013 | Black |
| 2014/0296917 A1 | 10/2014 | Donner et al. |

* cited by examiner

OCCIPITAL-CERVICAL FIXATION EQUIPMENT

The present application is a National Phase Entry of PCT International Application No. PCT/IB2016/057103, which was filed on Nov. 24, 2016, and which claims priority to application Ser. No. 102015000080059 filed in Italy on Dec. 3, 2015, the contents of which are hereby incorporated by reference.

The present invention relates to a spinal fixation equipment, in particular to an occipital-cervical fixation equipment.

Therefore, the present invention finds particular application in the biomedical field and, especially, in the manufacturing of fixation systems for spinal surgery.

As known, the fixation equipment are used in orthopaedic surgery to stabilize bones such as those of the vertebral column, providing support in the event of damage to the vertebral column itself.

In spinal surgery, it is known to stabilize two or more vertebrae using bone fasteners, for example obtained with poly-axial screws, connected by means of bars. In particular in case of occipital-cervical connection, it is known the use of an occipital plate and two bars, which are fixed on the vertebral body by means of polyaxial screws.

This connection allows the occipital-cervical loads to be transferred through the two bars, while limiting the torsional movement of the concerned vertebrae.

The Applicant has found that in the case of large and widespread damage, especially to the cervical vertebrae, the known connection presents poor stability, for example in case of movements between occiput and cervical vertebrae. Moreover, the connection has a non-optimal torsional functionality and distribution of loads (for example, the occipital-cervical loads).

Therefore, the object of the present invention is to provide an occipital-cervical fixation equipment able to overcome at least one of the drawbacks of prior art mentioned above.

More precisely, the purpose of the present invention is to provide a vertebral fixation equipment, preferably an occipital-cervical fixation equipment, able to further stiffen the portion of the vertebral column subject to the fixing procedure, compared with the known connections, unloading in more points the forces exerted, for example, by the skull on the cervical vertebrae and improving the torsional and flexion-extension functionality of the whole assembly.

Moreover, object of this invention is providing a vertebral fixation equipment, preferably an occipital-cervical fixation equipment, easy to position and adjust.

Said objects are achieved by a vertebral fixation equipment, preferably an occipital-cervical fixation equipment, having the features of one or more of the following claims. The dependent claims correspond to some possible embodiments of the invention.

In particular, a transverse connector is provided comprising a central longitudinal bar and a cross bar associated with the central longitudinal bar. The transverse connector can be fixed, for example, to the occipital plate at an end of the occipital portion of the central longitudinal bar and to the bars of the standard connection at the cross bar.

Thanks to the transverse connector, stability can be improved, in particular in case of movements between occiput and cervical vertebrae. In fact, the transverse connector allows bypassing the damaged vertebrae, for example the damaged cervical vertebrae, creating a safe connection directly on the standard connection bars.

Moreover, the loads, for example the occipital-cervical loads, are transmitted through three longitudinal bars improving the distribution of the loads.

Finally, the transverse connector improves the torsional functionality of the whole assembly.

The technical task mentioned and the objects stated are substantially achieved by a vertebral fixation equipment, preferably an occipital-cervical fixation equipment, comprising the technical characteristics set out in one or more of the appended claims. The dependent claims correspond to possible different embodiments of the invention.

The term "end occipital portion" refers to a portion of one of the components of the equipment, preferably elongated in shape, arranged or adapted to be arranged towards the occiput of the patient. The occipital end portion comprises an extremity of the occipital end portion.

The term "vertebral extremity portion" refers to a portion of one of the components of the equipment, preferably elongated in shape, arranged or adapted to be arranged on the opposite side of the occiput of the patient. The vertebral end portion comprises an extremity of the vertebral end portion.

In accordance with a first aspect, the present invention relates to a vertebral fixation equipment, for example an occipital-cervical fixation equipment, comprising two lateral longitudinal bars suitable for being arranged in a sagittal direction alongside the spinous processes of the patient's vertebrae.

In case of occipital-cervical fixation equipment, an occipital plate is able to be fixed to an occipital portion of the skull of a patient.

Each lateral longitudinal bar extends between an occipital end portion and a vertebral end portion.

First fixation means are configured to fix in place the occipital end portion of each lateral longitudinal bar. In case of an occipital-cervical fixation equipment, preferably the first fixation means are configured to fix the occipital end portion of each lateral longitudinal bar and the occipital plate.

Second fixation means are configured to fix in place the vertebral end portion of each lateral longitudinal bar. In case of an occipital-cervical fixation equipment, preferably the second fixation means are configured to fix the vertebral end portion of each lateral longitudinal bar and a patient's vertebra.

The vertebral fixation equipment, for example, the occipital-cervical fixation equipment, comprises a transverse connector comprising a central longitudinal bar suitable for being arranged along the sagittal direction between two lateral longitudinal bars, and a cross bar associated with the central longitudinal bar. The cross bar extends, transversely to the central longitudinal bar, between two lateral end portions. The central longitudinal bar extends between an occipital end portion and an vertebral end portion.

Third fixation means are configured to secure in place the occipital end portion of the central longitudinal bar. In case of an occipital-cervical fixation equipment, preferably the third fixation means are configured to secure the occipital end portion of the central longitudinal bar to the occipital plate.

Fourth fixation means are configured to fix the lateral end portions of the cross bar respectively to one of two longitudinal lateral bars.

According to a second aspect, the present invention relates to a method for implanting a vertebral fixation equipment. Two lateral longitudinal bars are arranged in a sagittal direction alongside the spinous processes of the patient's vertebrae and fixed therein. A transverse connector, comprising a central longitudinal bar and a cross bar associated with the central longitudinal bar, is arranged so that the central longitudinal bar is disposed along the sagittal direction between the two longitudinal lateral bars. The central longitudinal bar extends between an occipital end portion and a vertebral end portion. The cross bar extends, transversely to the central longitudinal bar, between two lateral end portions.

Preferably, the occipital end portion of the central longitudinal bar is secured in the place. Preferably, the lateral end portions of the cross bar are respectively fixed to one of two longitudinal lateral bars.

While implanting an occipital-cervical fixation equipment, the method comprises the step of fixing an occipital plate to an occipital portion of the skull of a patient. The two lateral longitudinal bars are arranged in a sagittal direction alongside the spinous processes of the patient's vertebrae.

The occipital end portion of each lateral longitudinal bar is fixed to the occipital plate by means of the first fixation means.

The vertebral end portion of each lateral longitudinal bar is fixed to a patient's vertebra by means of the second fixation means.

The occipital end portion of the central longitudinal bar is fixed to the occipital plate by means of the third fixation means.

The lateral end portions of the cross bar are respectively fixed to one of two longitudinal lateral bars, by means of the forth fixation means.

In one or more of the above-mentioned aspects, the present invention can comprise one or more of the following features.

Preferably, the third fixation means comprise a receiving and fixing bowl, or "tulip". In case of an occipital-cervical fixation equipment, the bowl is coupled to the occipital plate. Preferably, the receiving and fixing bowl comprises a groove for the insertion of the occipital end portion of the central longitudinal bar.

Preferably, the bowl comprises a through opening defining a housing for a screw. Preferably, the through opening extends along a longitudinal transverse direction, for example perpendicular to a longitudinal direction along which the grooves extends.

Preferably, the through opening is adapted to be placed in communication with a fixation seat of the occipital plate to define an housing for an occipital screw.

Preferably, the through opening communicates with the groove for the insertion of the occipital end portion of the central longitudinal bar.

Preferably, the bowl comprises a fixing element, preferably a threaded fixing element, for fixing the occipital end portion of the central longitudinal bar, for example into the groove. The fixing element is preferably arranged on the opposite side of the through opening with respect to the occipital end portion of the central longitudinal bar. Preferably, the occipital end portion is suitable to define, when in use, a stop for the screw, in particular for the occipital screw.

Preferably, the bowl comprises a fixing plate, for example configured to be fixed to the occipital plate in case of an occipital-cervical fixation equipment. Preferably, the fixing plate is provided with a centering portion insertable, for example, in the occipital plate, for example in the fixing seat.

Preferably, the fixing plate comprises at least one projecting portion insertable in a recess of the occipital plate, for example.

Preferably, the cross bar extends perpendicularly relative to the central longitudinal bar.

Preferably, the central longitudinal bar is arranged in a central position with respect to the cross bar dividing it into two portions having equal length.

Preferably, the transverse connector is "T" shaped.

Preferably, the transverse connector can be bent, if necessary.

Preferably, the cross bar is bent or can be bent, if necessary.

Preferably, the central longitudinal bar is straight or can be curved, if necessary.

Preferably, the cross bar is mounted at the vertebral end portion of the central longitudinal bar, for example at a vertebral end of the central longitudinal bar.

Preferably, a coupling area between the cross bar and the central longitudinal bar comprises anti-rotation means. The anti-rotation means can for example be defined by a polygonal seat associated with the central longitudinal bar and by a polygonal portion associated to the cross bar. Alternatively, the anti-rotation means can for example be defined by a polygonal seat associated with the cross bar and by a polygonal portion associated to the central longitudinal bar.

Preferably, the transverse connector comprises a fixation pin interposed between the central longitudinal bar and the cross bar to prevent relative sliding thereof.

Preferably, the equipment comprises at least a clamp slidingly constrained, for example, to the cross bar and the respective lateral longitudinal bar. Still more preferably, at least the forth fixation means comprise, for each of the lateral end portions of the cross bar, a clamp constrained to the cross bar and the respective lateral longitudinal bar.

Preferably, the clamp comprises a main body.

Preferably, the clamp comprises at least a first and a second housing seat, for example formed inside the main body. The first and second seats are preferably adapted to receive respectively one of the longitudinal lateral bars and an lateral end portion of the cross bar.

Preferably, the clamp comprises tightening means for locking, for example, the cross bar and the respective lateral longitudinal bar in an operative position with respect to the main body and to prevent the relative movements thereof.

Preferably, the clamp comprises interference means for restraining the free sliding at least of the cross bar or the lateral longitudinal bar inside the respective housing seat.

Preferably, the first and the second housing seats are arranged on parallel planes and extend along axial directions transverse to each other.

Preferably, the first seat is defined by a partially open groove formed in the main body.

Preferably, the second seat comprises a through hole inside the main body.

Preferably, the first seat is in communication with the second seat.

Preferably, the interference means project inwardly of the first or the second seat.

Preferably, the interference means comprise an elastic element adapted to exert a pressure force against the cross bar. Preferably, the elastic element is a protruding wire spring within the second housing seat.

Preferably, the interference means and the tightening means act within a respective housing. Each housing preferably extends along a direction orthogonal to the axial extension direction of the first and the second seats.

These and other features, as well as their technical advantages, will become more apparent from the following exemplifying, and not limiting description of a preferred, and not exclusive embodiment of an occipital-cervical fixation equipment.

Such description will be set forth hereinafter with reference to the accompanying drawings given only as an example and not intended as a limitation, in which.

With reference to the attached figures, the number 1 globally indicates a vertebral fixation equipment, in particular an occipital-cervical fixation equipment. In the following, an occipital-cervical fixation equipment will be described.

The equipment 1 is adapted to the occipital-cervical connection, and then to be arranged between an occipital portion of the skull 100 of a patient and the vertebrae 101, in particular the cervical vertebrae. 102 indicates the spinous processes of the vertebrae, especially of the cervical vertebrae.

The equipment 1 comprises an occipital plate 2 adapted to be fixed to the occipital portion 100.

Preferably, the occipital plate 2, initially flat in shape, is shaped and curved according to the patient's anatomy.

In accordance with a possible embodiment, the occipital plate 2 presents a plurality of spikes 3, for example arranged along the edges of the occipital plate, configured and arranged so as to cling to the skullcap to ensure the primary stability and avoid the sliding of the plate itself.

In accordance with a possible embodiment, one or more lightening apertures 4 may be provided.

The occipital plate 2 also includes a fixing seat 5 adapted to receive an occipital screw 6 designed to secure the occipital plate 2 to the occipital portion 100.

The equipment 1 also includes two lateral longitudinal bars 7 adapted to be arranged in a sagittal direction "S" alongside the spinous processes 102 of the vertebrae 101.

Each lateral longitudinal bar 7 extends between an occipital end portion 7a and an vertebral end portion 7b.

8 indicates the first fixation means configured to fix the occipital end portion 7a of each bar 7 to the occipital plate 2.

Figure 1:
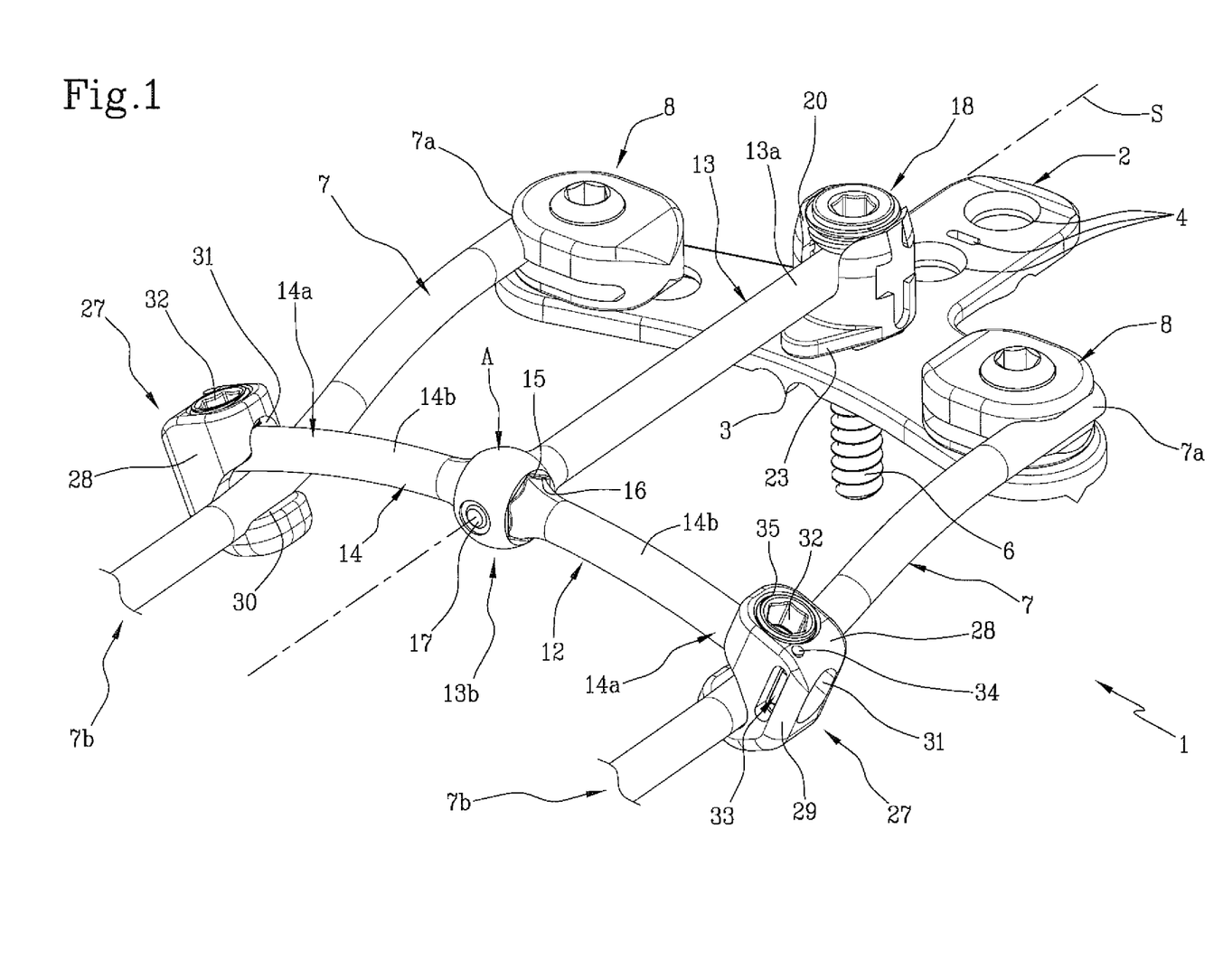
FIG. 1 is a perspective schematic view of an occipital-cervical fixation equipment according to the present invention.
Figures 2, 3:
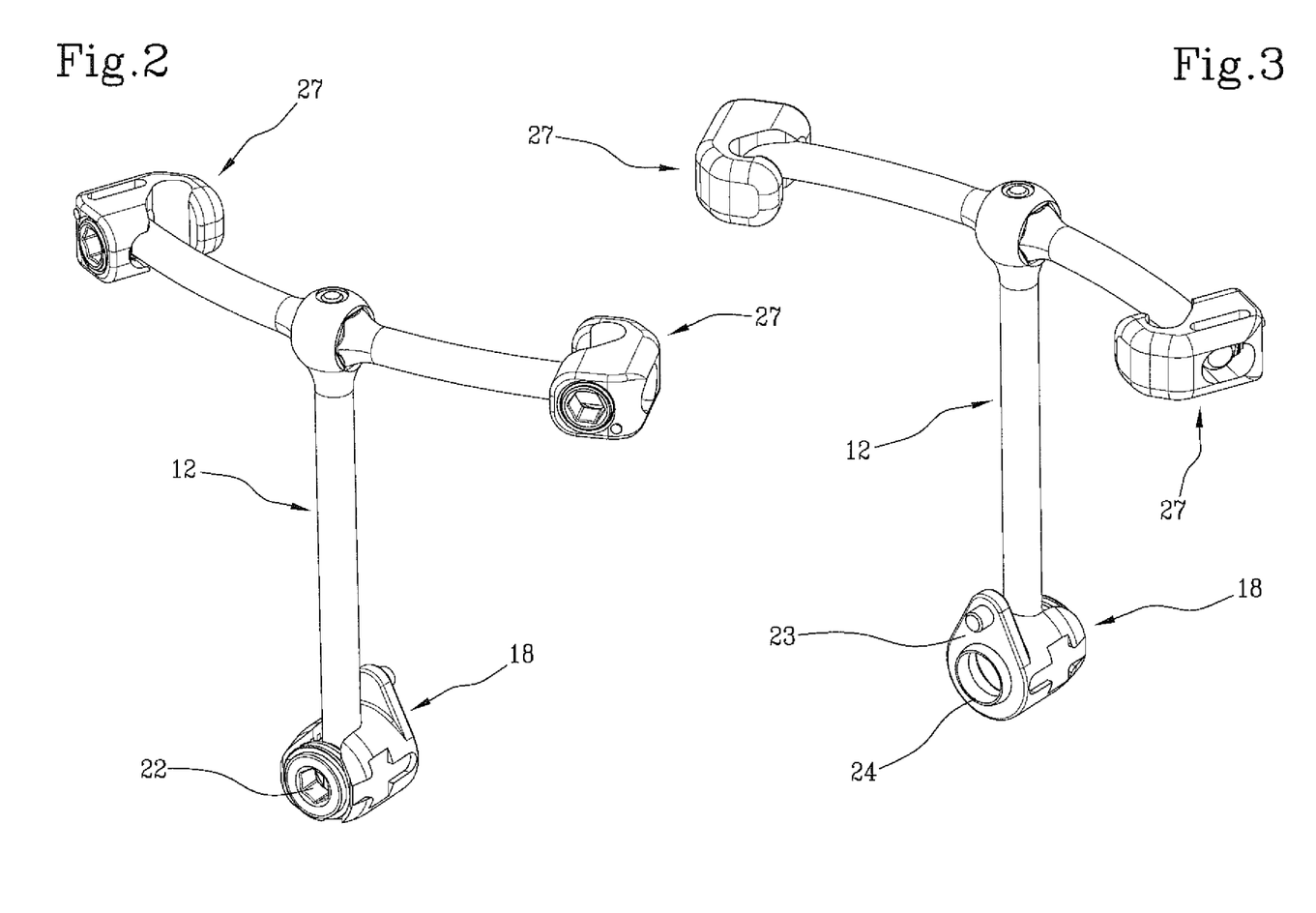
FIGS. 2 and 3 show each a schematic front and rear perspective view, of a portion of the equipment of FIG. 1.
Figure 4:
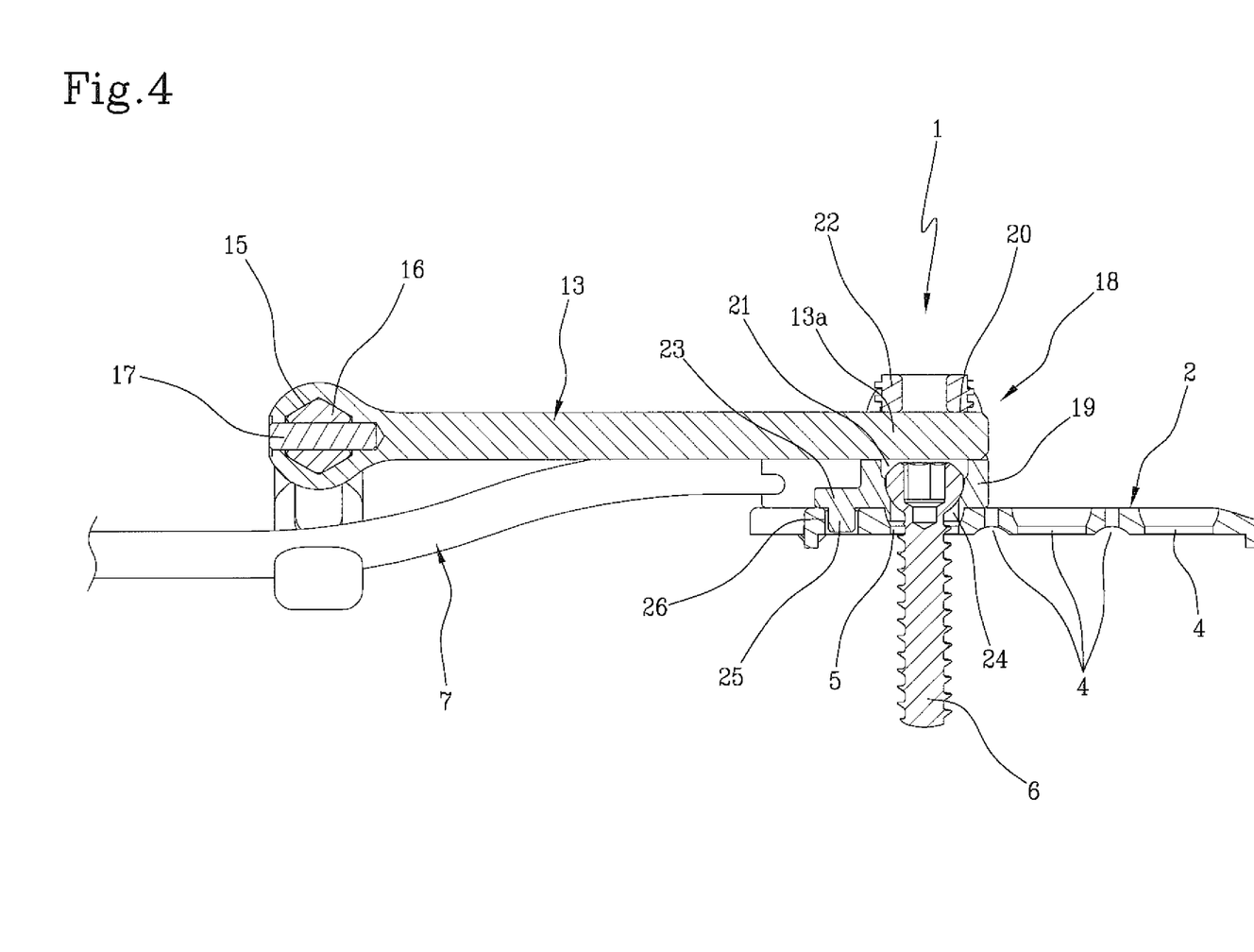
FIG. 4 shows a sagittal section of the equipment of FIG. 1.
Figure 5:
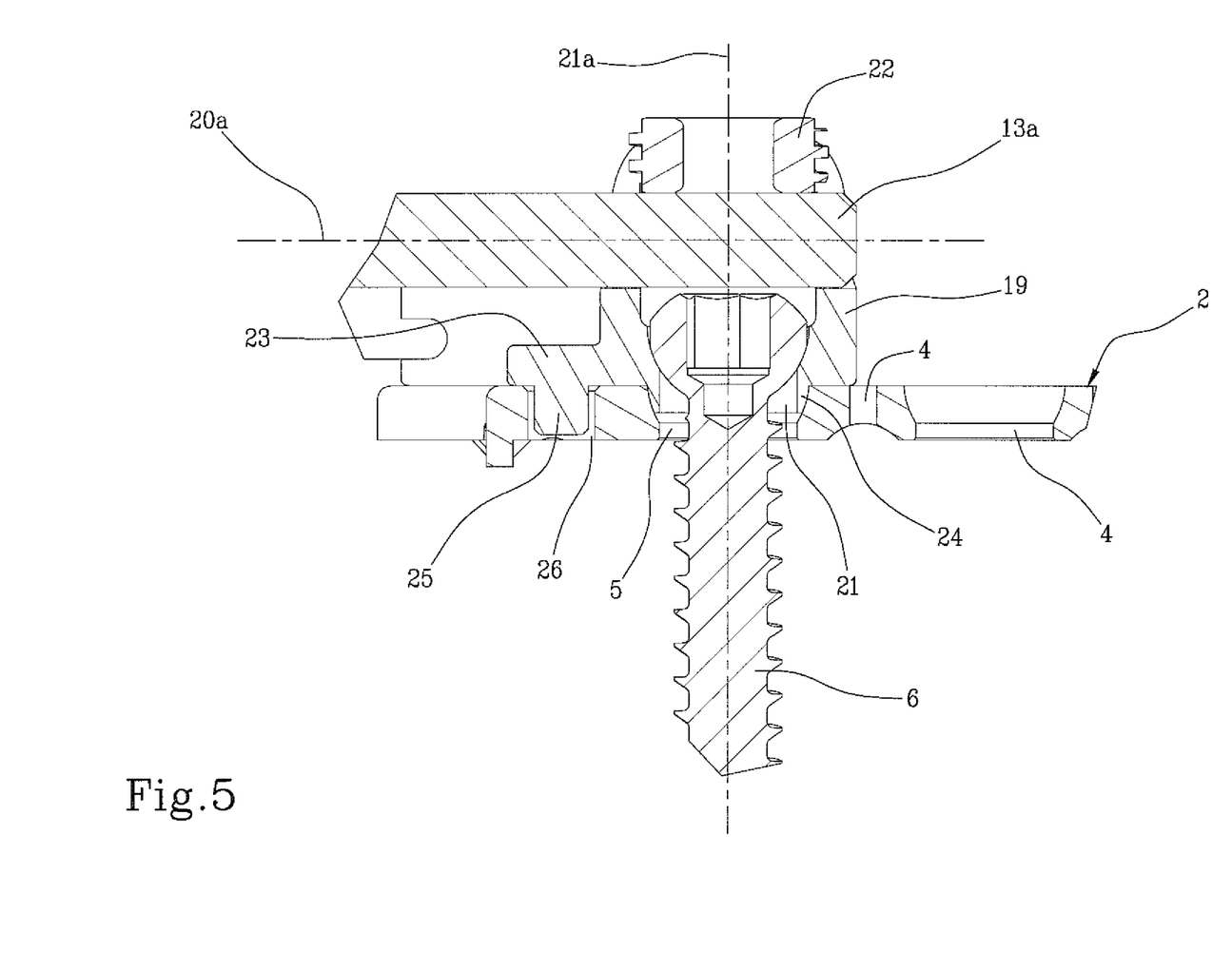
FIG. 5 shows an enlarged detail of FIG. 4.
Figure 6:
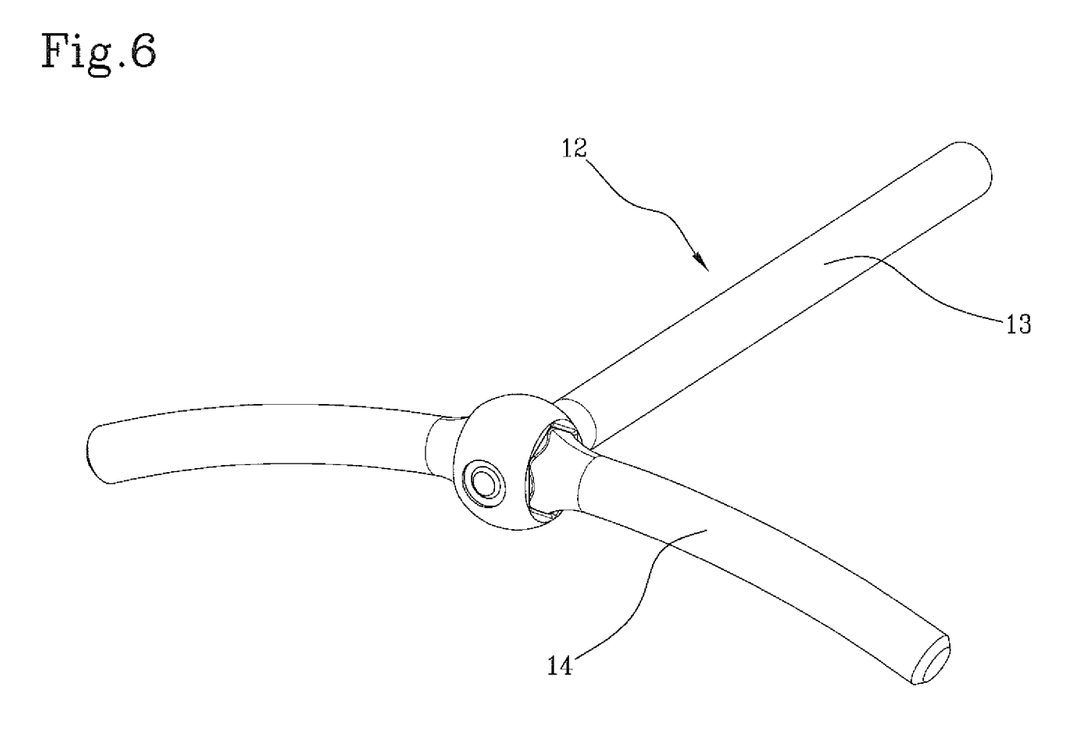
FIG. 6 shows a perspective view of a detail of the equipment of FIG. 1, 2 or 3.
Figure 7:
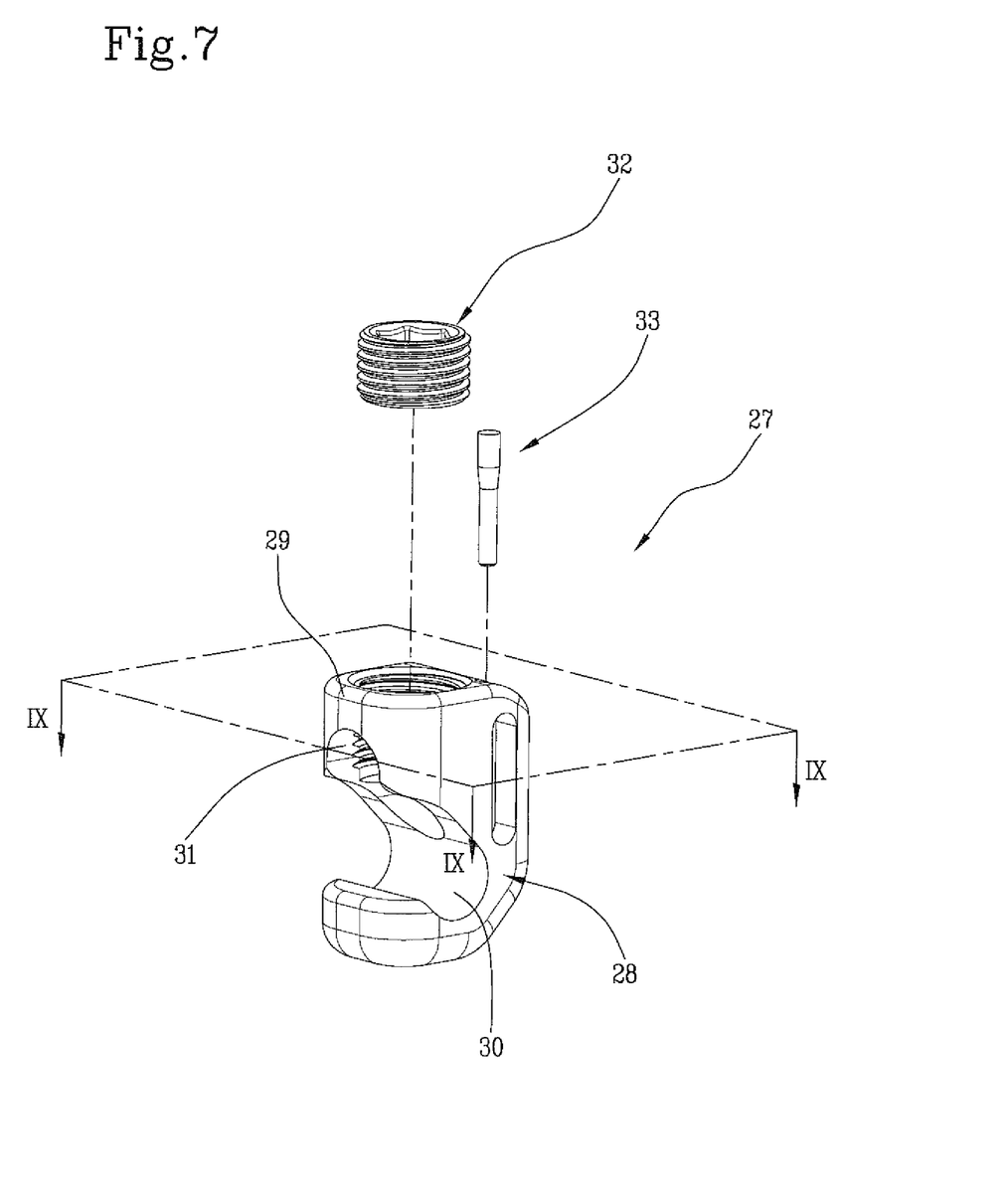
FIG. 7 shows a schematic perspective view of a detail of the equipment of FIG. 1, 2 or 3 with separated components.
Figure 8:
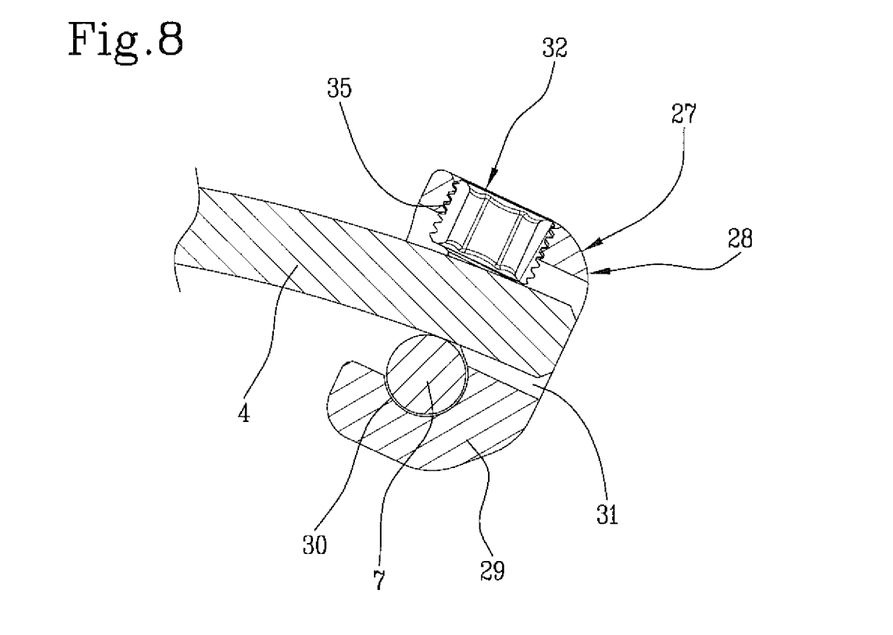
FIG. 8 and FIG. 9 shows sectional views of the detail of FIG. 7.
Figure 9:
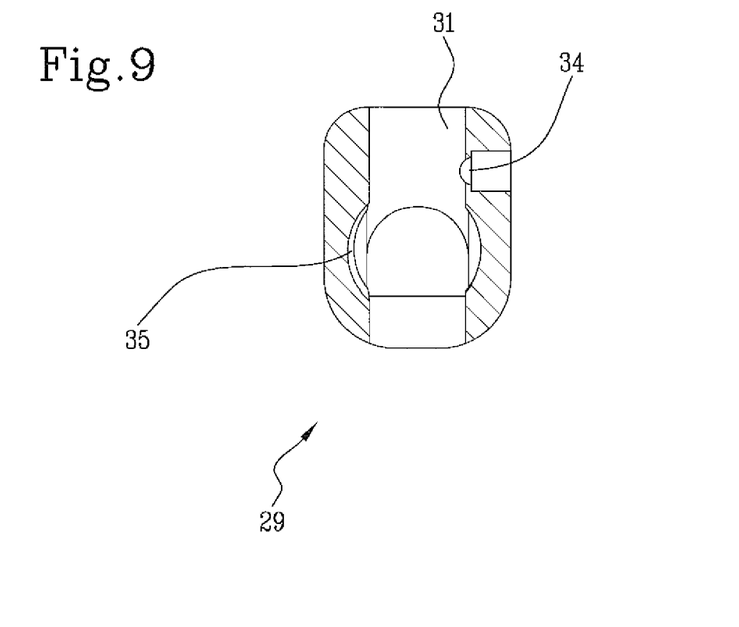
Figure 10:
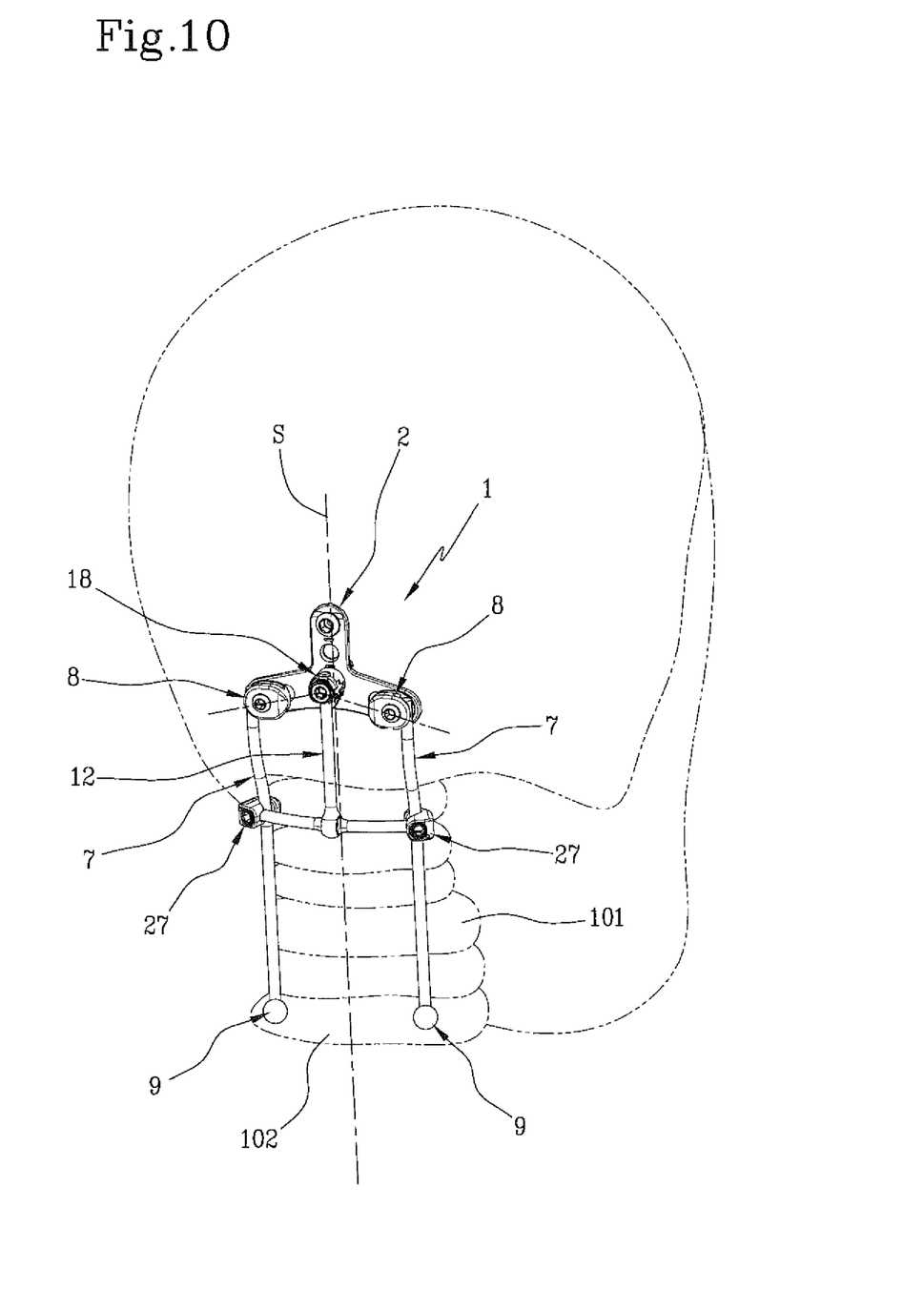
FIG. 10 shows a schematic view of a way of employment of the occipital-cervical fixation equipment of FIG. 1.

9 indicates the second fixation means, shown schematically in FIG. 10, configured to fix the bars 7 to a patient's vertebra. In case of severe damages to the cervical vertebrae, the second fixation means can be arranged in one of the lower vertebrae while providing stability and strength, as will be described below.

According to a possible embodiment, the second fixation means comprise polyaxial screws. An example of polyaxial screw is described and illustrated from page 8 to page 11 of the patent application MI2014A001383 by the Applicant.

12 indicates a transverse connector comprising a central longitudinal bar 13 and a cross bar 14 coupled with the central longitudinal bar 13, and arranged transversely to it. Preferably, the cross bar 14 extends perpendicularly relative to the central longitudinal bar 13.

Preferably, the central longitudinal bar 13 is arranged in a central position with respect to the cross bar 14 dividing it into two portions 14b having equal length.

Still more preferably, the transverse connector 12 is "T" shaped.

The central longitudinal bar 13 extends between an occipital end portion 13a and a vertebral end portion 13b. Preferably, the central longitudinal bar 13 is straight.

The cross bar 14 extends between two lateral end portions 14a.

Preferably, cross bar 14 is straight.

Preferably, the transverse connector 12 is made in two separate parts and assembled therebetween, each corresponding respectively to the central longitudinal bar 13 and to the cross bar 14. In this case, the cross bar 14 is preferably mounted at the extremity of the occipital end portion 13b of the bar 13. Still more preferably, the transverse rod 14 is mounted at a vertebral end of the bar 13.

In accordance with a possible embodiment, a coupling area "A" between the cross bar 14 and the central longitudinal bar 13 includes anti-rotation means, for example a polygonal seat 15 of the central longitudinal bar 13 and a polygonal portion 16 of the cross bar 14. Alternatively, the polygonal seat 15 may be coupled to the cross bar 14 and the polygonal portion 16 to the central longitudinal bar 13. Preferably, the transverse connector 12 comprises a fixation pin 17 interposed between the central longitudinal bar 13 and the cross bar 14, for example at the coupling area "A", to prevent relative sliding thereof.

In use, the central longitudinal bar 13 is arranged in the sagittal direction "S" between the two bars 7, and the cross bar 14 is arranged transversely to the bars 7, preferably in an area between the first fixation means 8 and second fixation means 9, so that the occipital end portion 13a lies at the occipital plate 2.

18 indicates the third fixation means configured to fix the occipital end portion 13a of the central longitudinal bar 13 to the occipital plate 2.

In accordance with a possible embodiment, third fixation means 18 comprise an receiving and fixing bowl 19, or "tulip", coupled with the occipital plate 2 and having a groove 20 for inserting the occipital end portion 13a of the central longitudinal said bar 13. The groove 20 extends along a longitudinal direction 20a.

Preferably, the bowl 19 comprises a through opening 21 adapted to be placed in communication with the fixation seat 5 of the occipital plate 2 defining an housing for the occipital screw 6. Still more preferably, the through opening 21 communicates with the groove 20.

The through opening 21 extends along a longitudinal direction 21a, preferably perpendicular to the longitudinal direction 20a along which the groove 20 extends.

22 indicates a fixing element, preferably a threaded fixing element, for fixing the occipital end portion 13a in the groove 20. The fixing element 22 is arranged on the opposite side of the through opening 21 with respect to the occipital end portion 13a so that, when in use, the occipital end portion 13a defines a stop for the occipital screw 6. When in use, the occipital end portion 13a is arranged perpendicularly to the occipital screw 6.

According to a possible embodiment, the bowl 19 comprises a fixing plate 23 provided with a centering portion 24 insertable into the fixing seat 5 of the occipital plate 2. The centering portion 24 is arranged around the through opening 21.

In accordance with a possible embodiment, the bowl 19 comprises a fixing plate 23 provided with at least a projecting portion 25 insertable in a recess 26 of the occipital plate 2 to prevent the rotation of the bowl 19.

27 refers to fourth fixation means configured to fix the lateral end portions 14*a* of the cross bar 14 respectively to one of two longitudinal lateral bars 7. Preferably, the forth fixation means 27 comprise, for each of the lateral end portions 14*a* of the cross bar 14, a clamp 28 slidably constrainable to the cross bar 14 and the respective lateral longitudinal bar 7.

Preferably, the clamp 28 comprises a main body 29 and at least a first housing seat 30 and a second housing seat 31, formed inside the main body 29. The first and second housing seat are able to receive respectively one of the lateral longitudinal bars 7 and the cross bar 14.

The clamp 28 comprises also tightening means 32 for locking the cross bar 14 and the respective lateral longitudinal bar 7 in an operative position with respect to the main body 29 and preventing the relative movements thereof.

The clamp 28 comprises also interference means 33 for restraining the free sliding at least of the cross bar 14 or the lateral longitudinal bar 7 within the respective housing seat.

The first and the second housing seats are arranged on parallel planes and extend along axial directions transverse to each other.

Preferably, the first seat 30 is defined by a partially open groove formed in the main body 29.

Preferably, the second seat 31 comprises a through hole within the main body 29.

The first seat 30 is in communication with the second seat 31.

Preferably, the interference means 33 project inwardly of the first 30 or the second 31 seat. Preferably, the interference means 33 comprise an elastic element able to exert a pressure force against the cross bar 14. Preferably, the elastic element is a protruding wire spring within the second housing seat 31.

Preferably, the interference means 33 and the tightening means 32 act inside a respective housing 34, 35, each extending along a direction orthogonal to the axial extension direction of the first and said second seats.

The transverse connector connects the occiput and the cervical vertebrae through the central longitudinal bar. The cross bar ensures the connection with the cervical implant by means of the two clamps 28. The transverse connector bypasses the damaged cervical vertebrae creating a safe connection directly on the longitudinal lateral bars.

Furthermore, the occipital-cervical loads are transmitted through three bars generating a better distribution of loads, in particular of sagittal forces.

When in use, the occipital plate is shaped and curved according to the patient's anatomy. The spikes, if any, ensure the primary stability, preventing them from slipping on the skullcap. Once constrained, the plate is connected to the lateral longitudinal bars through adjustable clamps, for example.

Before the system is completely locked, an adjustment of the clamps 28 along the cross bar and the lateral longitudinal bars allows the best fit to the system.

In the general case of a vertebral fixation equipment, the two lateral longitudinal bars 7 and the transverse connector 12 are provided, for example.

The first fixation means 8 are configured to secure in place, for example at a vertebra, the end occipital portion 7*a* of each lateral longitudinal bar 7.

The second fixation means 9 are configured to fix in place the vertebral end portion 7*b* of each lateral longitudinal bar 7 to a patient's vertebra.

The third fixation means 18 are configured to fix in place the occipital end portion 13*a* of the central longitudinal bar 13, for example in correspondence of a transverse connection between the two lateral longitudinal bars 7.

The fourth fixation means 27 are configured to fix the lateral end portions 14*a* of the cross bar 14 respectively to one of two longitudinal lateral bars 7.

The embodiments described above with reference to the occipital-cervical fixation equipment shall also apply to this possible aspect of the invention, especially the embodiments corresponding to one or more of the dependent claims envisaged for the occipital-cervical fixation equipment.

The invention claimed is:

1. Occipital-cervical fixation equipment comprising:
    an occipital plate able to be fixed to an occipital portion of the skull of a patient;
    at least two longitudinal lateral bars that are arrangeable in a sagittal direction alongside the spinous processes of the vertebrae of the patient, each longitudinal lateral bar extending between an occipital end portion and a vertebral end portion;
    a first fixation component configured to fix the occipital end portion of each longitudinal lateral bar and the occipital plate;
    a second fixation component configured to fix each of the longitudinal lateral bars to a patient's vertebra;
    a transverse connector comprising:
        a central longitudinal bar that is arrangeable according to the sagittal direction between the two longitudinal lateral bars, the central longitudinal bar extending between an occipital end portion and a vertebral end portion, and
        a cross bar associated with the central longitudinal bar and extending transversely thereto between two lateral end portions;
    a third fixation component configured to fix the occipital end portion of the central longitudinal bar to the occipital plate; and
    a fourth fixation component configured to fix each of the lateral end portions of the cross bar to a respective one of the two longitudinal lateral bars,
    wherein the at least two longitudinal lateral bars prevent flexion and extension of the patient's vertebrae between the first fixation component and the second fixation component.

2. The occipital-cervical fixation equipment according to claim 1, wherein the third fixation component comprises a receiving and fixing bowl or "tulip" coupled with the occipital plate and comprising a groove for inserting the occipital end portion of the central longitudinal bar.

3. The occipital-cervical fixation equipment according to claim 2, wherein the bowl comprises a through opening in communication with a fixation seat of the occipital plate to define a housing for an occipital screw.

4. The occipital-cervical fixation equipment according to claim 3, wherein the through opening communicates with the groove for inserting the occipital end portion of the central longitudinal bar.

5. The occipital-cervical fixation equipment according to claim 4, wherein the bowl comprises a threaded fixing element for fixing the occipital end portion of the central longitudinal bar within the groove, the fixing element being arranged on the opposite side of the through opening with respect to the occipital end portion of the central longitudinal bar, whereby the occipital end portion is able to define, when in use, a stop for the occipital screw.

6. The occipital-cervical fixation equipment according to claim 3, wherein the bowl comprises a fixing plate provided with a centering portion insertable into the fixation seat of the occipital plate.

7. The occipital-cervical fixation equipment according to claim 1, wherein the cross bar extends perpendicularly to the central longitudinal bar.

8. The occipital-cervical fixation equipment according to claim 1, wherein the central longitudinal bar is arranged centrally with respect to the cross bar dividing the cross bar into two portions having equal length.

9. The occipital-cervical fixation equipment according to claim 1, wherein the transverse connector has a "T" shape.

10. The occipital-cervical fixation equipment according to claim 1, wherein the cross bar is curved and/or the central longitudinal bar is straight.

11. The occipital-cervical fixation equipment according to claim 1, wherein the cross bar is mounted at the vertebral end portion of the central longitudinal bar, at a vertebral end of the central longitudinal bar.

12. The occipital-cervical fixation equipment according to claim 11, wherein a coupling zone between the cross bar and the central longitudinal bar includes an anti-rotation component.

13. The occipital-cervical fixation equipment according to claim 1, wherein the fourth fixation component includes, for each lateral end portion of the cross bar, a clamp slidably constrainable to the cross bar and a respective one of the longitudinal lateral bars, wherein said clamp comprises:
   a main body;
   at least a first and a second housing seats, formed within said main body and suitable to receive one of the longitudinal lateral bars and the cross bar, respectively;
   a tightening component which locks the cross bar and the respective lateral longitudinal bar in an operative position with respect to said main body and to prevent the relative movements thereof; and
   an interference component which restrains the free sliding at least of the cross bar or the lateral longitudinal bar inside the respective housing seat.

14. The occipital-cervical fixation equipment according to claim 13, wherein the first and the second housing seats are arranged on parallel planes and extend along axial directions transverse to each other.

15. The occipital-cervical fixation equipment according to claim 13, wherein the first seat is defined by a partially open groove formed in the main body.

16. The occipital-cervical fixation equipment according to claim 13, wherein the second seat comprises a through hole inside the main body.

17. The occipital-cervical fixation equipment according to claim 13, wherein the first seat is in communication with the second seat.

18. The occipital-cervical fixation equipment according to claim 13, wherein the interference component projects within said first or said second seat.

19. The occipital-cervical fixation equipment according to claim 13, wherein the interference component and the tightening component act inside a respective housing, each extending along a direction orthogonal to the axial extension direction of the first and the second seats.

20. Vertebral fixation equipment comprising:
   at least two longitudinal lateral bars that are arrangeable in a sagittal direction to the sides of the spinous processes of the vertebrae of the patient, each longitudinal lateral bar extending between an end occipital portion and an end vertebral portion;
   a first fixation component configured to secure in place the end occipital portion of each lateral longitudinal bar;
   a second fixation component configured to secure in place the end vertebral portion of each lateral longitudinal bar to a patient vertebra;
   a transverse connector comprising:
      a central longitudinal bar that is arrangeable according to the sagittal direction between the two longitudinal lateral bars, the central longitudinal bar extending between an end occipital portion and an end vertebral portion, and
      a cross bar associated with said central longitudinal bar and extending transversely thereto between two end side portions;
   a third fixation component configured to secure in place the end occipital portion of the central longitudinal bar; and
   a fourth fixation component configured to fix said end side portions of the cross bar respectively to one of two longitudinal lateral bars,
   wherein the at least two longitudinal lateral bars prevent flexion and extension of the vertebrae of the patient between the first fixation component and the second fixation component.

\* \* \* \* \*